United States Patent
Edvinsson et al.

(10) Patent No.: US 10,428,010 B2
(45) Date of Patent: Oct. 1, 2019

(54) PROCESS TO CONVERT CYCLIC ALKYLENE UREAS INTO THEIR CORRESPONDING ALKYLENE AMINES

(71) Applicant: Akzo Nobel Chemicals International B.V., Arnhem (NL)

(72) Inventors: Rolf Krister Edvinsson, Partille (SE); Eike Nicolas Kantzer, Uddevalla (SE); Per Fredrik Olmo Larsson, Göteborg (SE); Karl Fredrik Lake, Södertälje (SE); Antoon Jacob Berend Ten Kate, Arnhem (NL); Ulf Schröder, Lysekil (SE); Johan Salman Malmberg, Stockholm (SE)

(73) Assignee: Nouryon Chemicals International B.V., Arnhem (NL)

( * ) Notice: Subject to any disclaimer, the term of this patent is extended or adjusted under 35 U.S.C. 154(b) by 0 days.

(21) Appl. No.: 16/074,494

(22) PCT Filed: Feb. 10, 2017

(86) PCT No.: PCT/EP2017/052944
§ 371 (c)(1),
(2) Date: Aug. 1, 2018

(87) PCT Pub. No.: WO2017/137529
PCT Pub. Date: Aug. 17, 2017

(65) Prior Publication Data
US 2019/0039994 A1    Feb. 7, 2019

(30) Foreign Application Priority Data
Feb. 12, 2016    (EP) .................... 16155546

(51) Int. Cl.
*C07C 209/62* (2006.01)
*C07D 233/36* (2006.01)
*C07C 211/14* (2006.01)
*C07C 211/18* (2006.01)

(52) U.S. Cl.
CPC .......... *C07C 209/62* (2013.01); *C07D 233/36* (2013.01); *C07C 211/14* (2013.01); *C07C 211/18* (2013.01)

(58) Field of Classification Search
CPC ... C07C 209/62; C07C 211/14; C07C 211/18; C07D 233/36
See application file for complete search history.

(56) References Cited

U.S. PATENT DOCUMENTS

| | | |
|---|---|---|
| 2,812,333 A | 11/1957 | Steele |
| 4,387,249 A | 6/1983 | Harnden et al. |
| 4,503,250 A | 3/1985 | Herdle |
| 4,514,379 A | 4/1985 | Miller |
| 4,650,906 A | 3/1987 | Murakami et al. |
| 4,683,337 A | 7/1987 | Budde |
| 5,491,263 A | 2/1996 | Rooney et al. |

FOREIGN PATENT DOCUMENTS

| | | | |
|---|---|---|---|
| CN | 102952020 | * | 3/2013 |
| JP | S60-120842 A | | 6/1985 |
| JP | S60-126248 A | | 7/1985 |

OTHER PUBLICATIONS

English Translation of CN102952020, pp. 1-4, Mar. 2013.*
Xiaoping Chen et al., "Synthesis of Novel Polymer/Urea Peptoid Conjugates Using RAFT Polymerization", Macromolecules 2010, vol. 43, No. 3; Feb. 9, 2010, pp. 1341-1348, XP 055241030.
Notification of Transmittal of the International Search Report and the Written Opinion of the International Searching Authority, or the Declaration from the International Bureau of WIPO for International Application No. PCT/EP2017/052944 dated Apr. 21, 2017.
European Search Report issued in the counterpart European Application No. 16155546.1 dated Jun. 15, 2016.

* cited by examiner

*Primary Examiner* — Pancham Bakshi
*Assistant Examiner* — Mark R Luderer
(74) *Attorney, Agent, or Firm* — Norris McLaughlin, PA

(57) ABSTRACT

The present invention relates to a process to convert cyclic alkylene ureas into their corresponding alkylene amines wherein the process is performed by reaction with an amine compound, and wherein the amine compound comprises a primary amine, a cyclic secondary amine or a tertiary bicyclic amine.

15 Claims, 1 Drawing Sheet

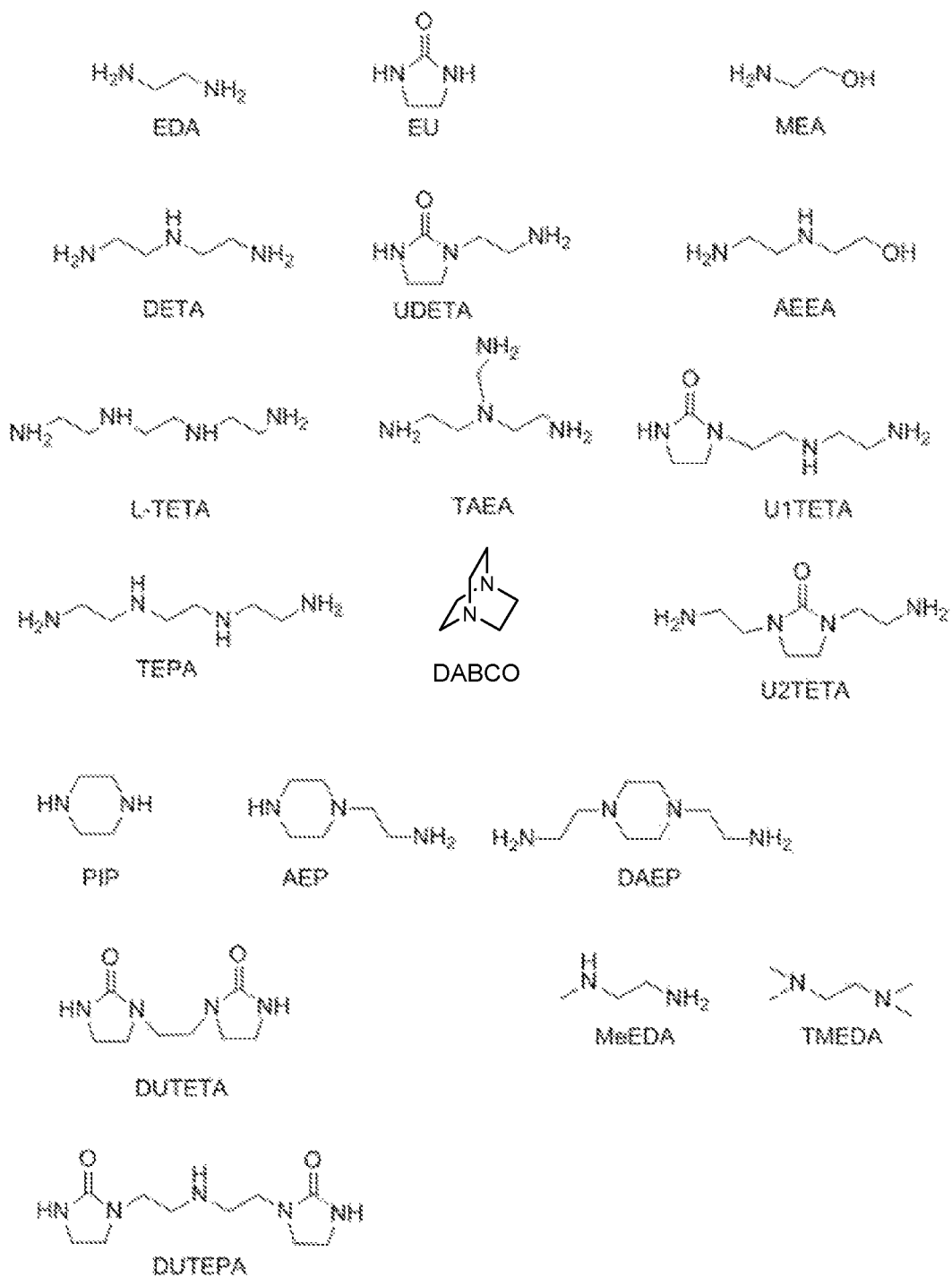

PROCESS TO CONVERT CYCLIC ALKYLENE UREAS INTO THEIR CORRESPONDING ALKYLENE AMINES

This application is a national stage filing under 35 U.S.C. § 371 of PCT/EP2017/052944, filed Feb. 10, 2017, which claims priority to European Patent Application No. 16155546.1, filed Feb. 12, 2016, the contents of which are each incorporated herein by reference in their entireties.

The present invention relates to a process to convert cyclic alkylene ureas into their corresponding alkylene amines

BACKGROUND

Two adjacent nitrogen atoms linked by one alkylene unit and one carbonyl moiety form a cyclic alkylene urea. When alkylene is ethylene, an ethylene amine (EA) in which two nitrogen atoms are linked intramolecular by a carbonyl moiety

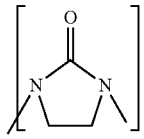

is here referred to as an UEA. Replacing the carbonyl bridge with two hydrogen atoms yields the corresponding ethylene amine. For example: EU↔EDA, UDETA↔DETA, UAEEA↔AEEA, UTETA↔L-TETA, UTEPA↔L-TEPA. Some higher amines host more than one carbonyl moiety, e.g. DUTETA the diurea of L-TETA. The carbonyl moiety may link nitrogen atoms on two separate molecules. For example $H_2NC_2H_4NH$—CO—$NHC_2H_4NH_2$ and replacing the carbonyl moiety with two hydrogen atoms here yields two EDA. As to naming of the molecules, EDA stands for ethylenediamine, DETA for diethylenetriamine, TETA for triethylenetetraamine, TEPA for tetraethylenepentamine, PEHA for pentaethylenehexamine, AEEA stands for aminoethylethanolamine. When there is a single cyclic urea in the molecule this is indicated by adding a U in front of the name, e.g. UTETA means the cyclic urea of TETA, while when there are two cyclic ureas in the molecule this is indicated by DU, i.e. DUTETA means the internal cyclic diurea of TETA. If there is a number indicated for the U this refers to the amino group where the U group is located. There is one exception to this naming and that is that instead of UEDA the abbreviation EU is used, which stands for ethyleneurea.

Aqueous solutions of alkylene and alkanol amines are commonly used in reversible $CO_2$ absorption processes. On absorption a range of compounds are formed such as carbonates, bicarbonates, carbamates and alkylene ureas. Desired products are those that readily desorb $CO_2$ on heating. Cyclic carbamates and ureas are undesirable owing to their high stability.

U.S. Pat. No. 4,650,906 and JP 60126248 disclose the decarboxylation of ethylene amine carbonates by heat treatment and distillation. Examples of carbonates disclosed are those of diethylenetriamine (DETA), triethylenetetramine (TETA), tetraethylenepentamine (TEPA), pentaethylenehexamine (PEHA), and piperazine (PIP). JP 60120842 discloses besides thermal treatment also the addition of a hydroxide-containing base. None of these two documents discloses cyclic alkylene ureas or a conversion thereof to give the corresponding alkylene amines.

U.S. Pat. No. 4,683,337 discloses the conversion of ethylene amines to linear carbamates by reacting them with $CO_2$ followed by decarbonating and dehydrating them to recover the amines. US '337 does not disclose the formation of cyclic alkylene ureas.

The process of the present invention as indicated is about converting cyclic alkylene ureas into their corresponding alkylene amines, more in particular it is about removing the carbonyl group of a cyclic alkylene urea to give the corresponding alkylene amine according to the following general reaction scheme:

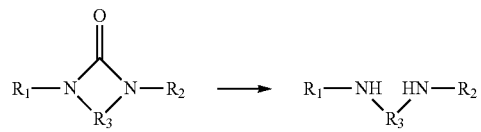

U.S. Pat. No. 4,387,249 discloses the reaction of ethylenediamine (EDA), ethanolamine (MEA) and urea to give aminoethylethyleneurea (UDETA) and ethyleneurea (EU) that after hydrolysis gives DETA and EDA. The hydrolysis is said to be done in the presence of a Brønsted base, but the only one specifically mentioned is sodium hydroxide.

U.S. Pat. No. 4,503,250 discloses the hydrolysis of a product mixture obtained by the reaction of an amine or ammonia with an alcohol in the presence of carbonic acid derivatives. In the examples work-up of the reaction mixture is performed using 50% aqueous KOH under reflux overnight. In the examples of '250 it can be seen that the yield of alkylene amines obtained by treating the reaction mixture with KOH is low and subject to improvement.

The use of caustic bases as disclosed by the prior art documents to remove the carbonyl group from cyclic alkylene ureas also has as a disadvantage that it results in low product selectivities due to degradation of the desired products. In addition, when using an (inorganic) base, salts are formed as by-products which complicate the following separation of organics, resulting in lower yields of the targeted product. In addition the combination of amines, water, salt and high temperatures can cause problems with corrosion, discolored products and decreased storage stability. Salt generation also creates waste.

The present invention provides a process in which the above problems are solved.

The present invention relates to a process to convert cyclic alkylene ureas into their corresponding alkylene amines wherein the process is performed by reaction with an amine compound and wherein the amine compound is a primary amine, a cyclic secondary amine or a bicyclic tertiary amine.

Unexpectedly, it was found that amines, which are much weaker bases than the inorganic caustic bases hitherto disclosed, are effective in converting cyclic alkylene ureas into their corresponding (linear) alkylene amines at high yields of the desired alkylene amine products and that degradation of the alkylene amines is minimized. It was also found that only certain amines are effective and that the chemical nature of the amine is critical to the function and not the basicity by itself, which shows that the mode of function is distinctly different from that of caustic bases like NaOH and KOH.

Unexpectedly, when using the amines of the present invention to convert cyclic alkylene ureas into their corresponding alkylene amines, the degradation of the alkylene amines is to a large extent avoided, and a much better yield of the desired alkylene amines is provided. It is believed that in the process of the invention the amine reactant does not primarily act as a base but as a nucleophile which makes the process distinctly different from the prior art processes using caustic for the conversion. Furthermore, the process of the invention is much less critical on dosing reactants because the amines are in embodiments, for example embodiments wherein water is present, not consumed by the process and additionally the process of the present invention has an advantage that water needs not be added in all embodiments, such as for example when alkylene and alkanol amines are employed and the respectively obtained cyclic alkylene urea and cyclic alkylene carbamate can be recovered as products. In many embodiments it is possible and advantageous to use reactive separation steps, for example reactive stripping or reactive distillation, to separate the alkylene amine from the cyclic alkylene urea in order to further the reaction to the product side, which process steps would be less desirable in the presence of hydroxides as heating reaction mixtures rich in hydroxides easily gives corrosion.

It should be noted that U.S. Pat. No. 4,514,379 discloses a catalytic process to convert oxazolidinones into alkanol amines by using a small amount of amine, preferably the alkanol amine precursor of the oxazolidinone. It is said that the use of a catalytic amount of amine will reduce or eliminate the need for a long induction period when using water without an inorganic base and it is suggested that waste is avoided in comparison to using an inorganic base. It is nowhere disclosed or suggested that the use of amines increases yields by preventing the formation of degradation products. Converting cyclic carbamate functionalized compounds into an alkanol amine is much easier than converting a cyclic urea functional compound into an alkylene amine, as cyclic carbamates are much more reactive and—in contrast to cyclic ureas—can be efficiently hydrolyzed with water alone. This would clearly lead someone to believe that using amine compounds for converting ureas would be an unacceptable alternative.

In a preferred embodiment in the process of the invention the cyclic alkylene urea that is subjected to the conversion to give a corresponding alkylene amine are:

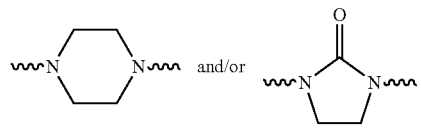

Wherein $R_1$ and $R_2$ each independently are chosen from the group of hydrogen, an alkylene amine group of the formula $X-R_3-(NH-R_3-)_p-$, or an alkoxy group of formula $X-R_3-(O-R_3-)_n-$, or a group combining such alkylene amine and alkoxy units p and n, wherein one or more units $\sim N-R_3-N\sim$ may be present as either one of the rings

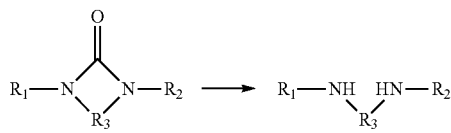

and wherein each $R_3$ independently is as defined below and X may be hydroxyl, amine, a linear or branched C1-C20 hydroxyalkyl or C1-C20 aminoalkyl group, n and p independently is at least 1, preferably 2-20, optionally containing one or more piperazine, or alkylene urea groups, or when p or n is 0 may be a C1-C20 hydroxyalkyl or C1-C20 aminoalkyl, and $R_3$ is alkylene or substituted alkylene.

In a preferred embodiment R2 is a hydrogen atom and R1 is not a hydrogen atom.

In a more preferred embodiment R2 is a hydrogen atom and R1 contains a repeating alkylene amine group, even more preferably a repeating ethylene amine group of the formula $X-(NH-C_2H_4)_n$ wherein optionally one or more units $NH-C_2H_4-NH$ may be present as one of the rings

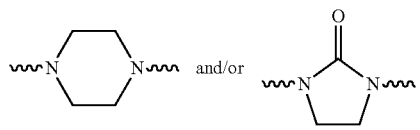

and wherein n is 1 to 20, and X may be a hydrogen atom, an aminoalkyl, an hydroxyalkyl, N-imidazolidinonealkyl or piperazinoalkyl group, most preferably wherein the alkyl is ethyl.

R3 is preferably ethylene or propylene, optionally substituted with C1-C3 alkyl substituents. More preferably it is an unsubstituted ethylene or propylene, most preferably ethylene.

Some examples of cyclic alkylene ureas that are most preferred are EU (ethyleneurea), UDETA (the urea of diethylenetriamine), UTETA (the ureas of triethylenetetraamine, i.e. U1TETA or U2TETA, dependent on whether the urea is between the $1^{st}$ and $2^{nd}$ amine in the chain or $2^{nd}$ and $3^{rd}$ amine, respectively), DUTETA (the diurea of triethylenetetramine), DUTEPA (the diurea of tetraethylenepentamine) or any mixture of these. The molecular structures of the above cyclic alkylene ureas are given in the FIGURE.

The amine compound can be a primary amine, a cyclic secondary amine or a bicyclic tertiary amine. Primary amines are amine functional compounds in which the amine group is of the formula $R4-NH_2$ and wherein R4 can be any organic group, preferably an aliphatic hydrocarbon with optional heteroatoms such as oxygen and/or nitrogen. Secondary cyclic amines are amines of the formula R5-NH-R6, wherein R5 and R6 together form a hydrocarbon ring, optionally with heteroatoms such as oxygen and/or nitrogen, preferably a piperazine ring. Tertiary bicyclic amines are amines of the formula R7-N(-R9)-R8 where R7 and R8 together form a hydrocarbon ring—optionally with heteroatoms such as oxygen and/or nitrogen—and R7 and R9 together form another hydrocarbon ring—optionally with heteroatoms such as oxygen and/or nitrogen. On all the above groups R4 to R9 substituents can be present, like alkyl or hydroxyalkyl groups. Primary amines, cyclic secondary amine and bicyclic tertiary amines all contain a sterically relatively unhindered amine group. In this document a compound is defined as a primary amine or a secondary cyclic amine or a tertiary bicyclic amine if one of the amine groups in the compound is a primary amine or secondary cyclic amine or a tertiary bicyclic amine group, independent of if this compound contains further amine groups that may be different in their nature. A compound can also contain two or more different amine functionalities, e.g. a primary amine and a secondary cyclic amine functionality or a primary amine, a secondary cyclic amine and a tertiary bicyclic amine functionality.

Preferred examples of primary amines are alkylamines, linear ethylene amines, and alkanolamines. Preferred examples of cyclic secondary amines are amines that contain a terminal piperazine ring. Preferred examples of bicylic tertiary amines are 1,4-diazabicyclo[2.2.2]octane (DABCO), 1,4-diazabicyclo[2.2.2]octan-2-yl)methanol and 1-azabicyclo[2.2.2]octane (Quinuclidine). Structures of some of the amine compounds are given in the FIGURE.

The amine compound is preferably a compound with more than one amine group wherein at least one of the amine groups is a primary amine, even more preferably it is an amine wherein two amine groups are a primary amine. The amine compound is preferably a compound different than R1-NH—R3-NH—R2 that is obtained by the process of the invention.

In another preferred embodiment the amine compound is a compound that can bind with the carbonyl group from the cyclic alkylene urea (CAU). Preferred amine compounds include an alkylene amine, or an alkanol amine compound, even more preferably a smaller alkylene amine, ethylene amine, or alkanol amine, ethanolamine, than is formed by the process of the invention, most preferably EDA or DETA, MEA, aminoethylethanolamine (AEEA), N-aminoethylpiperazine (AEP), N, N'-diaminoethylpiperazine (DAEP), UDETA, N, N'-diaminoethyl-2-imidazolidinone (U2TETA), tris-aminoethylamine (TAEA). Many of the above compounds are shown in the FIGURE.

In yet another preferred embodiment the amine compound is a compound that binds the carbonyl group from the cyclic alkylene urea to give among others another linear or cyclic alkylene urea or linear or cyclic alkylene carbamate, that is larger or less volatile than the alkylene amine formed by the process of the invention, even more preferably an ethylene amine that is solid under the conditions used to work up the reaction mixture or an ethylene amine bound to a solid carrier. Examples thereof are DETA-PS (i.e. a diethylene triamine linked to a solid polystyrene) or a solid polyethyleneimine (PEI).

The process of the present invention can be done with or without any additional liquid present. If a liquid is added to the reaction system, the liquid preferably is a polar liquid, such as an alcohol or water. Doing the process of the present invention in the presence of water as a liquid or without any liquid is preferred. Since in some preferred embodiments the amine compound will react to yield another, in preferred embodiments less stable, urea or carbamate compound, having water present during the reaction can have the additional benefit that the newly formed urea compound can be hydrolyzed with water to release its carbonyl group which can then be recycled into the process or separated off, for example as carbon dioxide or a ionic derivative thereof (such as hydrogen carbonate or carbonate salt).

The amine compounds that are preferably used when the reaction is done in the presence of water are ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), 1,4-diazabicyclo[2.2.2]octane (DABCO), 1,4-diazabicyclo[2.2.2]octan-2-yl)methanol, triethylenetetramine (TETA), N-diethyldiamine-2-imidazolidinone (U1TETA), N,N'-diaminoethylpiperazine (DAEP), N,N'-diaminoethyl-2-imidazolidinone (U2TETA), tetraethylenepentamine (TEPA), pentaethylenehexamine (PEHA), and the mono cyclic ureas of TEPA and PEHA (i.e. U1TEPA, U2TEPA, U1PEHA, U2PEHA, U3PEHA) and the dicyclic urea isomers of PEHA (i.e. DUPEHA), a polyethyleneimine (PEI) or an alkylene amine on a solid carrier.

In a further preferred embodiment the released carbonyl group, i.e. often carbon dioxide, is continuously removed from the process which will enhance the process. The carbon dioxide can be removed for example by working in a suitable reactor unit comprising or connected to a section for actively removing $CO_2$ by desorption, for instance by distillation, stripping or flashing, with or without a membrane.

In preferred embodiments the above subsequent step of hydrolyzing a potentially formed cyclic or non-cyclic urea to releasing carbon dioxide is performed by at least a step in which the materials are stripped. A person skilled in the art will know that such a stripping step is suitably done by having a sufficiently high flow of carrier gas and by ensuring good mixing and proper gas to liquid contact so that the maximum amount of carbon dioxide is removed from the system, in any way, the carbon dioxide should be so removed or isolated that it will not recombine with the amine compound with which it originally formed the cyclic urea, or any other amine compound.

In another preferred embodiment of the invention the amine compound or any urea compound formed from the reaction between the amine compound and the cyclic urea compound are recycled back into the process or separated off.

The process of the invention is preferably done at a temperature of at least 150° C., preferably at least 200° C., more preferably at least 230° C., and most preferably of at least 250° C. Preferably the temperature during the process does not exceed 400° C., more preferably 350° C.

The process of the present invention is in embodiments is performed for a time of between 1 minute and 12 hours. Preferably the reaction is run in less than 10 hours, more preferably in less than 8 hours, most preferably less than 5 hours. As a skilled person will understand this reaction time does not include any further processing of the reaction mixture such as for separating the obtained compounds.

The process can be carried out in a batch reactor, possibly fed-batch operation, or in a continuously operating system such as in a cascade of continuous flow reactor. The reaction and separation can be performed in separate steps or at least partially simultaneously.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

In such a scheme, the cyclic alkylene urea, amine compound and possibly water may be fed to the equipment as desired at a single point or at multiple points throughout the process equipment, which may include continuously stirred tank reactors, tubes, pipes, reactive distillation columns, reactive stripping units or combinations thereof.

The person skilled in the art is capable of selecting the proper reactor and separation unit scheme by determining the overall yield, energy consumption and waste production.

The amine compound is preferably dosed in a molar amount of between 0.001 and 100 equivalents in regard to the total molar amount of CAU, more preferably between 0.01 and 50 equivalents, even more preferably between 0.05 and 30 equivalents, yet more preferably between 0.15 and 25 equivalent and most preferably between 0.20 and 20 equivalents.

In a most preferred embodiment a cyclic alkylene urea of TETA or TEPA, such as linear TETA diurea (DUTETA) or linear TEPA diurea (DUTEPA), is converted to linear TETA (L-TETA) or linear TEPA (L-TEPA) by employing EDA, DETA, MEA, AEEA, N-methyl EDA (MeEDA), AEP, DAEP, U2TETA, TAEA with or without added water.

Particularly preferred are the amine compounds EDA, DETA, U2TETA, DAEP or AEP when doing the reaction in the presence of water The conversion of DUTETA with EDA and water proceeds preferably between 150 and 350° C., preferably between 200 and 300° C.

EXAMPLES

Example 1; Conversion of DUTETA to L-TETA Using EDA (a Primary Amine) in the Presence of Water 1.0 g (5.05 mmol) DUTETA was added to 6 g (100 mmol) EDA and 6 g water (330 mmol) and heated to 260° C. in a closed pressure vessel for 3 h. Analysis by gas chromatography using a flame ionization detector (GC-FID analysis) showed the formation of 0.68 g L-TETA (92% of the theoretical yield), 0.06 g of U2TETA, and 0.04 g of U1TETA. No remaining DUTETA was determined.

Comparative Example 2; Conversion of DUTETA Using 50% KOH in Water for 15 Hours 3.0 g (15.1 mmol) DUTETA was added to 27.2 g (242 mmol) 50% aqueous KOH and heated to reflux in a round bottom flask with attached cooler at atmospheric pressure for 15 hours to resemble the conditions as presented in U.S. Pat. No. 4,503,250 (reflux temperature, reacted overnight). GC-FID analysis of the resulting product mixture did not detect L-TETA. The remaining material contained mainly DUTETA and some non-analyzed decomposition products.

Comparative Example 3; Conversion of DUTETA to L-TETA Using 50% KOH in Water for 3 Hours 3.0 g (15.1 mmol) DUTETA was added to 27.2 g (242 mmol) 50% aqueous KOH and heated to reflux in a round bottom flask with attached cooler at atmospheric pressure for 3 hours to resemble the conditions as presented in U.S. Pat. No. 4,503,250 but now using the reaction time of Example 1. GC-FID analysis showed the formation of 0.15 g L-TETA (6.8% of the theoretical yield) after 3 h. The majority of the remaining material was DUTETA.

Example 4; Conversion of DUTETA to L-TETA Using EDA (a Primary Amine) without Added Water 3.0 g (15.1 mmol) DUTETA was added to 12 g (200 mmol) EDA and heated to 250° C. for 1 h in a closed pressure vessel. GC-FID analysis showed the formation 0.72 g L-TETA (33% of the theoretical yield), 1.46 g of U1TETA, and 0.20 g of U2TETA. 0.17 g of DUTETA remained.

Comparative Example 5; Conversion of DUTETA to U1TETA with N,N,N',N'-Tetramethyl EDA (TMEDA) (a Non-Cyclic Tertiary Amine) in the Presence of Water 4.0 g (20.2 mmol) DUTETA was added to 7.3 g of water (404 mmol) and 9.4 g of TMEDA, (80.7 mmol), and the mixture was heated to 260° C. for 3 h in a closed pressure vessel. GC-FID analysis showed the formation of 0.06 g of L-TETA (2.0% of the theoretical yield), 0.62 g U1TETA, and 0.17 g of U2TETA, while 2.9 g of DUTETA remained.

The low yield of L-TETA using TMEDA shows that sterically hindered tertiary amines do not give as good results as e.g. EDA (Example 1), even using an excess of TMEDA.

Example 6; Conversion of DUTETA Using PIP (a Cyclic Secondary Amine) in the Presence of Water 3.0 g (15.1 mmol) DUTETA was added to 15 g of water (830 mmol) and 3.0 g of PIP (34.8 mmol), and the mixture was heated to 250° C. for 2 h in a closed pressure vessel. GC-FID analysis showed the formation of 0.16 g of L-TETA (7.2% of the theoretical yield), 1.1 g of U1TETA, and 0.49 g of U2TETA, while 1.2 g of DUTETA remained.

Converting DUTETA to L-TETA and U1TETA using PIP proves that also amines which cannot form stable cyclic urea intermediates can be successfully used.

Example 7; Conversion of DUTETA to U1TETA Using 1,4-Diazabicyclo[2.2.2]octane (DABCO) (a Tertiary Bicyclic Amine) in the Presence of Water 3.0 g (15.1 mmol) DUTETA was added to 15 g of water (830 mmol) and 3.0 g of DABCO (26.7 mmol), and the mixture was heated to 250° C. for 2 h in a closed pressure vessel. GC-FID analysis showed the formation of 0.06 g of L-TETA (2.7% of the theoretical yield), 1.1 g of U1TETA, and 0.47 g of U2TETA, while 1.2 g of DUTETA remained.

DABCO shows a fair DUTETA conversion.

Example 8; Conversion of DUTETA to L-TETA Using AEP (a Primary Amine but Also a Cyclic Secondary and a Cyclic Tertiary Amine) in the Presence of Water 4.0 g (20.2 mmol) DUTETA was added to 7.3 g of water (404 mmol) and 10.4 g of AEP (1-(2-Aminoethyl)piperazine, 80.7 mmol), and the mixture was heated to 260° C. for 3 h in a closed pressure vessel. GC-FID analysis showed the formation of 0.71 g of L-TETA (24% of the theoretical yield), 1.7 g U1TETA, and 0.47 g of U2TETA, while 0.79 g of DUTETA remained.

As was also demonstrated in Example 6, even compounds which cannot form stable cyclic ureas—such as AEP—are active in the conversion of DUTETA.

Example 9A to F, Conversion of DUTETA to L-TETA Using Different Amines Dosed by Weight 2.0 g (10 mmol) DUTETA, 6.0 g of the respective amine as represented in Table 1 below, and 6.0 g of water (333 mmol) were added to a pressure vessel which was heated at 250° C. for 2 h. The results of the GC-FID analyses are summarized in Table 1.

The following amine compounds were tested:

DMEDA, 3-MPA

-continued

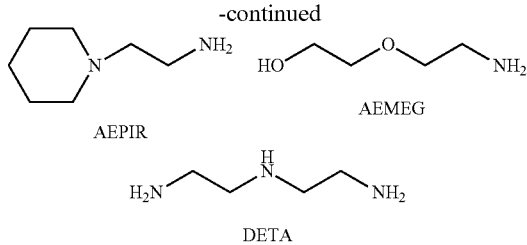

DMEDA: N',N'-dimethyl-1,2-ethanediamine,
3-MPA: 3-methoxy-1-propanamine,
AEPIR: 1-Piperidineethanamine
AEMEG: 2-(2-aminoethoxy)-ethanol

TABLE 1

Results for: DUTETA + amine + H₂O (1/3/3 by weight); 250° C., 2 h.

| | Example | | | | | |
|---|---|---|---|---|---|---|
| | 9A | 9B | 9C | 9D | 9E | 9F |
| | Amine compound | | | | | |
| | EDA | DMEDA | 3-MPA | AEPIR | AEMEG | DETA |
| Amount of amine compound in mmol | 99.8 | 68.1 | 67.3 | 46.8 | 57.1 | 58.2 |
| EDA | 84.3 | 0.3 | n.d. | 1.7 | 0.3 | 1.0 |
| EU | 4.3 | n.d. | n.d. | n.d. | n.d. | n.d. |
| L-TETA | 10.9 | 5.5 | 3.1 | 4.7 | 5.9 | 15.7 |
| ΣUTETAs | 8.9 | 11.1 | 10.2 | 11.0 | 11.1 | 4.8 |
| DUTETA | 1.6 | 4.3 | 7.4 | 6.0 | 4.3 | n.d. |
| DMEDA | | 67.0 | | | | |
| 3-MPA | | | 69.8 | | | |
| AEPIR | | | | 79.1 | | |
| AEMEG | | | | | 81.5 | |
| DETA | | | | | | 70.2 |
| UDETA | | | | | | 23.8 |
| L-TETA yield (% of theory) | 53 | 33 | 18 | 24 | 30 | 74 | all data in above table if not specified otherwise are given in wt %
ΣUTETAs denotes the sum of U1TETA and U2TETA
n.d. = below detection limits The results demonstrate that various types of amines according to the invention can be used to convert cyclic ureas.

Example 10A-D; Conversion of DUTETA to L-TETA Using Different Amines Dosed by mmol 2.0 g (10 mmol) DUTETA, 100 mmol of the respective amine as represented in Table 2 below (including g of each amine), and 6.0 g water (333 mmol) were added to a pressure vessel which was heated at 250° C. for 2 h. The results of the GC-FID analysis are summarized in Table 2.

In addition to EDA, DETA and AEMEG, also 1,3-diaminopropylamine (PDA) was tested.

TABLE 2

Results for: DUTETA + amine + H₂O (1/10/33 by mol); 250° C., 2 h.

| Example | 10A | 10B | 10C | 10D |
|---|---|---|---|---|
| Amine compound | EDA | PDA | DETA | AEMEG |
| Amount of amine compound in g | 6.0 | 7.5 | 10.4 | 10.6 |
| EDA | 84.3 | n.d. | n.d. | n.d. |
| EU | 4.3 | n.d. | n.d. | n.d. |
| L-TETA | 10.9 | 10.2 | 10.8 | 2.1 |
| ΣUTETAs | 8.9 | 4.8 | 2.0 | 6.0 |
| DUTETA | 1.6 | 0.7 | n.d. | 4.4 |
| PDA | | 80.2 | | |
| UPDA | | 8.7 | | |
| DETA | | | 80.1 | |
| UDETA | | | 18.4 | |
| AEMEG | | | | 84.2 |
| L-TETA yield (% of theory) | 53 | 62 | 81 | 18 | all data in above table if not specified otherwise are given in wt %
n.d. = below detection limits The results demonstrate that the reaction can be performed using different relative amounts of an amine compound.

Example 11A-11C, Conversion of DUTETA to L-TETA Using EDA. Effect of a Stripping Gas for Removing CO₂

DUTETA (104 g, 0.525 mol), EDA (322 g, 5.35 mol) and water (322 g, 17.9 mol) were charged to a pressure autoclave equipped with internal temperature control, mechanical overhead stirring, a condenser with a pressure regulator on top, and a stripping gas sparger connected to a dip pipe at the bottom of the reactor. The autoclave was put under an atmosphere of nitrogen and then the temperature was ramped up during 45 minutes. The mixture was heated at 250° C. for 7 h without (Example 11A) or with N₂ stripping gas (Examples 11B and 11C). The stripping gas was introduced using a sparger with ca 3 mm inner diameter ports or 2 μm inner diameter ports (Examples 11B and 11C, respectively). The results are shown in Table 3.

TABLE 3

Results for stripping with $N_2$: DUTETA + amine + $H_2O$ (1/3/3 by weight); 250° C., 7 h

| Example | 11A | 11B | 11C |
|---|---|---|---|
| Conditions | no stripping | $N_2$ stripping, 3 mm sparger | $N_2$ stripping, 2 μm sparger |
| L-TETA | 10.2 | 58.4 | 70.9 |
| DUTETA | n.d. | n.d. | n.d. | all data in above table if not specified otherwise are given in wt %
n.d. = below detection limits It was demonstrated that stripping off $CO_2$ while converting DUTETA into L-TETA leads to higher L-TETA yields. As evidenced by the result using a sparger with 2 μm ports compared to using a sparger with 3 mm ports, a better gas-to-liquid contact helps to further improve L-TETA yields.

The invention claimed is:

1. Process to convert cyclic alkylene ureas into their corresponding alkylene amines wherein the process is performed by reaction with an amine compound, and wherein the amine compound is chosen from the group of primary amines, cyclic secondary amines or bicyclic tertiary amines;
wherein the cyclic alkylene urea reacts to the corresponding alkylene amine in accordance with below reaction

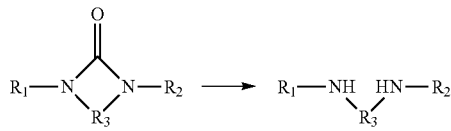

wherein $R_1$ and $R_2$ each independently are chosen from the group of hydrogen, an alkylene amine group of the formula X—$R_3$—(NH—$R_3$—)$_p$—, or an alkoxy group of formula X—$R_3$—(O—$R_3$—)$_n$—, or a group combining such alkylene amine and alkoxy units p and n, wherein optionally one or more units ~N—$R_3$—N~ may be present as either one of the rings

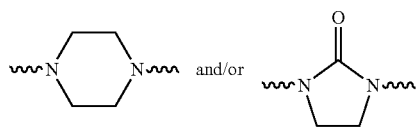

and wherein each $R_3$ independently is alkylene or substituted alkylene, X may be hydroxyl, amine, a linear or branched C1-C20 hydroxyalkyl or a linear or branched C1-C20 aminoalkyl group, n and p independently are 0 or at least 1, wherein when n and/or p is at least 1 the linear or branched C1-C20 hydroxyalkyl or C1-C20 aminoalkyl croup optionally contains one or more piperazine or alkylene urea groups.

2. Process of claim 1 wherein the amine compound is a compound that can bind the carbonyl group from the cyclic alkylene urea to give another linear or cyclic alkylene urea or linear or cyclic alkylene carbamate.

3. Process of claim 2 wherein the amine compound is a smaller alkylene amine or alkanol amine than the one derived from the starting cyclic alkylene urea after the conversion.

4. Process of claim 2 wherein the amine compound is an alkylene amine or an alkanol amine compound that is larger than the one derived from the starting cyclic alkylene urea after the conversion.

5. Process of claim 3 wherein the amine compound is ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), N-diethyldiamine-2-imidazolidinone (U1TETA), N, N'-diaminoethylpiperazine (DAEP), N, N'-diaminoethyl-2-imidazolidinone (U2TETA), a polyethyleneimine (PEI) or an alkylene amine on a solid carrier.

6. Process of claim 1 wherein the reaction is done in the presence of a polar liquid.

7. Process of claim 1 wherein the amine compound is ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), 1,4-diazabicyclo[2.2.2]octane (DABCO), 1,4-diazabicyclo[2.2.2]octan-2-yl)methanol, triethylenetetramine (TETA), N-diethyldiamine-2-imidazolidinone (U1TETA), N, N'-diaminoethylpiperazine (DAEP), N, N'-diaminoethyl-2-imidazolidinone (U2TETA), tetraethylenepentamine (TEPA), pentaethylenehexamine (PEHA), and the mono cyclic ureas of TEPA and PEHA (i.e. U1TEPA, U2TEPA, U1 PEHA, U2PEHA, U3PEHA) and the dicyclic urea isomers of PEHA, a polyethyleneimine (PEI) or an alkylene amine on a solid carrier, and the reaction is done in the presence of water.

8. Process of claim 1 wherein the reaction is done at a temperature of at least 150° C.

9. Process of claim 1 wherein the amine compound is added to the process in a molar amount of between 0.15 and 25 equivalent based on the total molar amount of cyclic alkylene urea.

10. Process of claim 1 containing a subsequent step wherein any urea compound formed from reaction between the amine compound and the cyclic urea compound is hydrolyzed with water to release its carbonyl group to provide carbon dioxide or an ionic derivative thereof.

11. Process of claim 10 wherein the carbon dioxide or ionic derivative thereof are recycled back into the process or separated off.

12. Process of claim 1 wherein the amine compound or any urea compound formed from reaction between the amine compound and the cyclic urea compound are recycled back into the process or separated off.

13. Process of claim 4 wherein the amine compound is ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), N-diethyldiamine-2-imidazolidinone (U1TETA), N, N'-diaminoethylpiperazine (DAEP), N, N'-diaminoethyl-2-imidazolidinone (U2TETA), a polyethyleneimine (PEI) or an alkylene amine on a solid carrier.

14. Process of claim 1 wherein n and p independently are at most 20.

15. Process of claim 6 wherein the polar liquid is water.

* * * * *